United States Patent [19]
Martinique

[11] Patent Number: 5,661,850
[45] Date of Patent: Sep. 2, 1997

[54] EYE SHIELD ASSEMBLY

[76] Inventor: Robert Martinique, 537 Avenue A, Apt. 228, Bayonne, N.J. 07002

[21] Appl. No.: 658,669

[22] Filed: Jun. 4, 1996

[51] Int. Cl.$^6$ ............................................. A61F 9/04
[52] U.S. Cl. ................................. 2/15; 128/858; 602/74
[58] Field of Search ...................... 2/15; 602/74; 128/858

[56] References Cited

U.S. PATENT DOCUMENTS

| | | | |
|---|---|---|---|
| 2,389,223 | 11/1945 | Werner | 2/15 |
| 2,643,382 | 6/1953 | McLeod | 2/15 |
| 4,677,974 | 7/1987 | Leonardi | 602/74 |
| 4,682,371 | 7/1987 | Heltman | 128/858 |
| 4,709,695 | 12/1987 | Kohn et al. | 128/858 |
| 4,850,376 | 7/1989 | DellaVecchia et al. | 2/15 |
| 4,898,162 | 2/1990 | Worthrich | 2/15 |
| 4,969,472 | 11/1990 | Langley et al. | 2/15 |
| 5,183,059 | 2/1993 | Leonardi | 2/15 |

*Primary Examiner*—Michael A. Neas
*Attorney, Agent, or Firm*—Louis E. Marn

[57] ABSTRACT

There is disclosed an eye shield assembly comprised of an ovate-shaped cup assembly defining a chamber for positioning over an eye socket of a user wherein the chamber is of a depth sufficient to be in non-contacting relationship with the associated eyelash thereof and wherein end members are mounted to the ovate-shaped cup member and include an end portion having a hook member and an end portion having a loop member for cooperation in interlocking relationship with the hook member of the other end member and wherein each end portion is formed of an elastic material. The ovately-shaped cup member is formed with an elliptically-shaped upper edge having a major curved portion proximate a nose of the user and an elliptically-shaped lower edge having a major curved portion remote from the nose of the user thereby defining an asymmetrical relationship between the upper and lower edges.

6 Claims, 2 Drawing Sheets

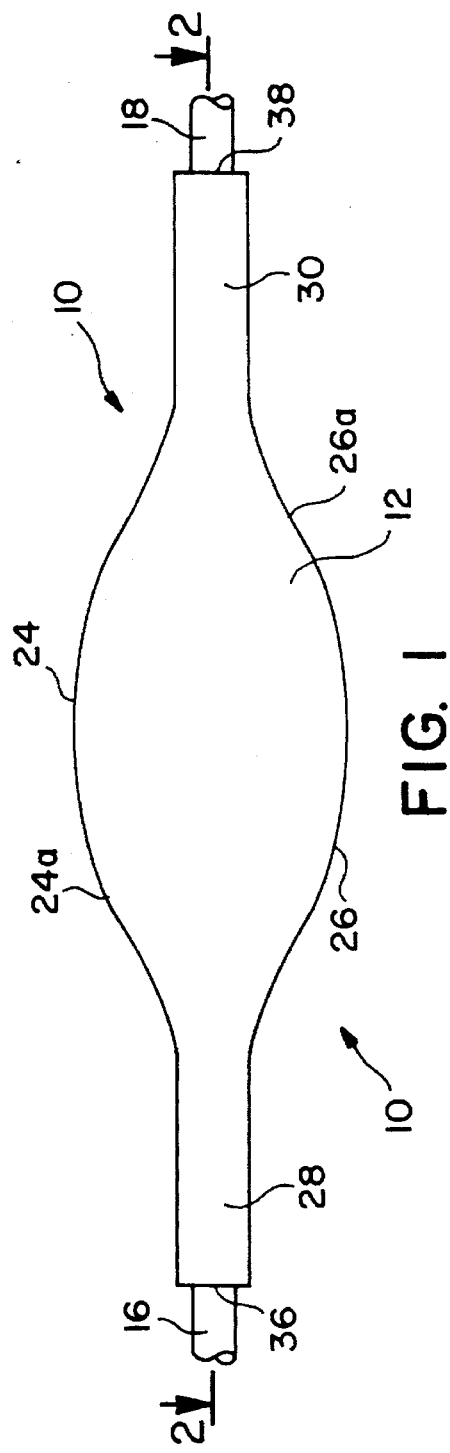
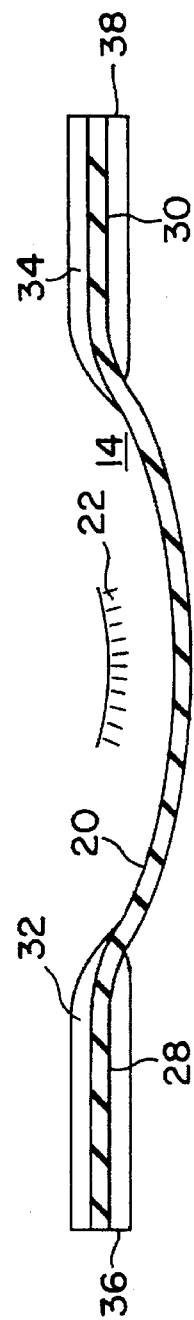
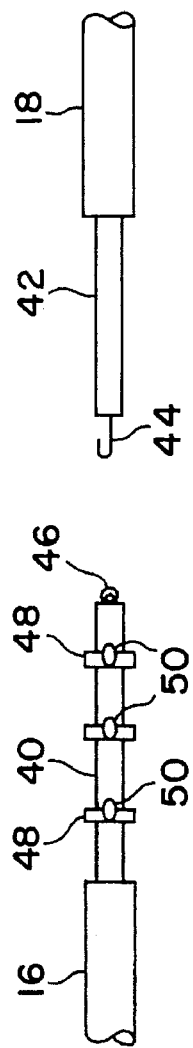

EYE SHIELD ASSEMBLY

BACKGROUND OF THE INVENTION

1. Field of the Invention

This invention relates to an improved eye shield assembly and more particularly to an improved eye shield assembly permitting of improved air circulation.

2. Description of the Prior Art

Eye shields have been the subject matter of a plethora of Letters Patents, e.g., U.S. Pat. No. 591,244 to Wylie, U.S. Pat. No. 1,161,321; U.S. Pat. No. 2,389,223 to Werner and the like. While all systems have obviated problems, there is the need for an attractively styled eye shield with concomitant features to permit facile adjustable attachment while compensating for hair growth and head growth, as well as improved air circulation.

OBJECT OF THE PRESENT INVENTION

An object of the present invention is to provide an improved eye shield assembly having facile head positioning and mounting assembly.

Another object of the present invention is to provide an improved eye shield assembly compensating for hair growth and head growth.

Still another object of the present invention is to provide an improved eye shield assembly of comfortable fitting to substantially ease migraines.

Yet another object of the present invention is to provide an improved eye shield assembly permitting of air circulation.

A still further object of the present invention (additional objects).

SUMMARY OF THE INVENTION

These and other objects of the present invention are achieved by an eye shield assembly comprised of an ovately-shaped cup assembly defining a chamber for positioning over an eye socket of a user wherein the chamber is of a depth sufficient to be in non-contacting relationship with the associated eyelash thereof and wherein end members are mounted to the ovate-shaped cup member and include an end portion having a hook member and an end portion having a loop member for cooperating in interlocking relationship with the hook member of the other end member and wherein each end portion is formed of an elastic material. The ovately-shaped cup member is formed with an elliptically-shaped upper edge having a major curved portion proximate a nose of the user and an elliptically-shaped lower edge having a major curved portion remote from the nose of the user thereby defining an asymmetrical relationship between the upper and lower elliptically-shaped edges.

BRIEF DESCRIPTION OF THE DRAWINGS

A better understanding of the present invention as well as other objects and advantages thereof will become apparent upon consideration of the detailed disclosure thereof, especially when taken with the accompanying drawings wherein:

FIG. 1 is a partial elevational front view of the improved eye shield assembly of the present invention for positioning about a left eye of a user;

FIG. 2 is a partial cross-sectional top view of the eye shield assembly taken along the lines 2—2 of FIG. 1;

FIG. 3 is one end portion of the eye shield assembly;

FIG. 4 is the other end portion of the eye shield assembly; and

DETAILED DESCRIPTION OF THE INVENTION

Figure 5:
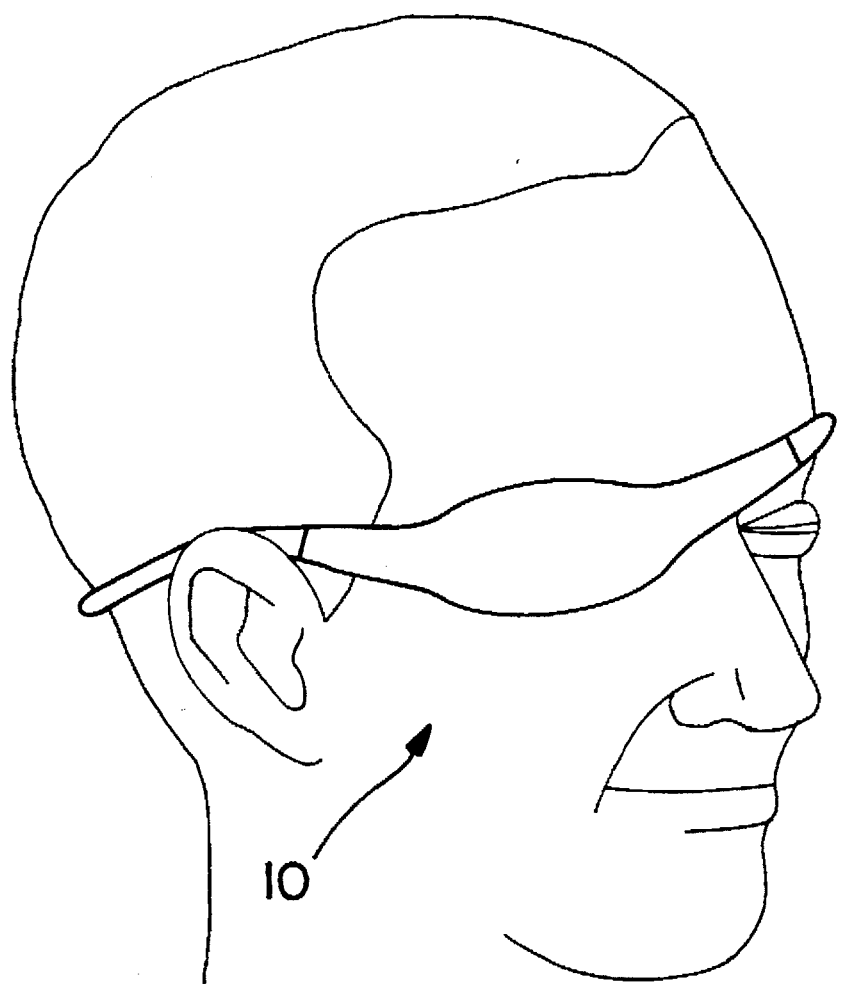
FIG. 5 is a front view with the eye shield assembly in place on a head of a user.

Referring now to the drawings, there is illustrated an eye shield assembly, generally indicated as 10, for covering an eye of a user, referring specifically to FIG. 5. The eye shield assembly 10 is comprised of an ovately-shaped body shell member 12 defining a chamber 14 and extending to end member 16 and 18. The shell body member 12 may be formed of leather or like synthetic material with an inner surface 20 of the shell member 12 defining the chamber 14 formed to a depth to be positioned over the eye socket of the user such that eyelash 22 of the covered eye does not contact the inner surface 20 of the shell body 12 thereby preventing irritation by eyelash contact with such inner surface 20.

The shell body member 12 is formed with an elliptically-shaped upper edge 22 and an elliptically-shaped lower edge 24 with a major curved portion 24A and a major curved portion 26A of the upper and lower edges 24 and 26 being asymmetrically disposed with respect to each other. The major curved portion 24A of the upper edge 24 is positioned remote from the nose of the user defining the asymmetrical relationship with a major curved portion 26A of the lower edge 26 proximate the nose of the user. The upper and lower edges 24 and 26 of the shell body member 12 taper to end portions 28 and 30, respectively.

The upper edge 24 is configured to be in part displaced from or not in non-contacting relationship with the upper eyelid of the covered eye to permit air circulating within the chamber 14 of shell member 12. The end portions 28 and 30 are upturned at lower sections 32 and 34 thereof, respectively, to accommodate close fitting relationship with the temple and bridge of the nose, respectively, of the user.

The end portions 28 and 30 terminate at end points 36 and 38, respectively, with end members 16 and 18 being affixed thereto, such as by sewing. The end members 16 and 18 include strap members 40 and 42 mounted to the end portions 16 and 18 and formed of an elastic material. Strap portion member 42 of the end member 18 is provided with a hook member 44, as more fully hereinafter described. The end strap member 40 of the end member 16 is provided with an end loop member 46 and intermediate anchors 48 in which are mounted intermediate hook members 50 for engagement with the hook member 44 of the end member 42 once proper fitting relationship is found by the user, as more fully hereinafter described.

In operation, the ovately-shaped cup member 12 of the eye shield assembly is positioned about the right eye of the user with the end members 16 and 18 brought about the temple and crossed over the top of each ear. The hook member 44 of the strap member 42 is thereupon caused to engage one of the loop members 46/50 of the strap member 40 as a function of comfortable fit. When properly positioned, the ovate cup member 12 is disposed over the eye socket such that a portion of the upper edge 24 is proximate but not in contacting relationship with the head of the user. It is understood that an eye shield assembly 10 for positioning about the left eye of a user would be in mirror image construction, i.e., the major curved portion 24A of the upper edge 22 would be remote from the nose of the user and asymmetrically disposed to the major curved portion 26A of the lower edge 26.

While the invention has been described in connection with an exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed is:

1. An eyeshield assembly for covering an eye, which comprises:

an ovately-shaped cup member defining a chamber of a dept sufficient to be in non-contacting relationship with a user' eyelash and having an elliptically-shaped upper edge asymmetrically disposed to an elliptically-shaped lower edge;

a first end member mounted to an end of said ovately-shaped cup member having a hook member mounted thereto and a second end member mounted to the other end of said ovately-shaped cup member and having a loop member for cooperating in interlocking relationship with said hook member of said first end member.

2. The eye shield member as defined in claim 1 wherein said elliptically-shaped upper edge is formed with a major curve portion remote from a nose of a user with said elliptically-shaped lower edge formed with a major curve portion proximate from said nose of said user.

3. The eye shield assembly as defined in claim 2 wherein said upper edge is formed to include a portion spaced apart from the forehead of the user in position to provide air circulation about a covered eye.

4. The eye shield assembly as defined in claim 2 wherein said end members include elastic members on which are mounted said hook and loop members.

5. The eye shield assembly as defined in claim 2 wherein said second end member is provided with a plurality of spaced-apart loop members.

6. The eye shield assembly as defined in claim 2 wherein said ovate cup member is formed of leather.

* * * * *